United States Patent [19]

Cockley

[11] Patent Number: 5,757,460
[45] Date of Patent: May 26, 1998

[54] COMBINATION OPHTHALMIC DEVICE

[76] Inventor: Thomas D. Cockley, 555 Iron Hill Rd., Doylestown, Pa. 18901

[21] Appl. No.: 710,390

[22] Filed: Sep. 16, 1996

[51] Int. Cl.$^6$ .................................................. A61B 3/10
[52] U.S. Cl. ........................ 351/205; 351/204; 351/213
[58] Field of Search ............................... 351/244, 200, 351/205, 245, 204, 213, 214

[56] References Cited

U.S. PATENT DOCUMENTS

| | | | |
|---|---|---|---|
| 1,158,187 | 10/1915 | De Zeng | 351/200 |
| 2,526,493 | 10/1950 | McCoy | 351/205 |
| 3,724,931 | 4/1973 | Nevyas et al. | 351/214 |
| 5,139,326 | 8/1992 | Snider | 351/205 |
| 5,202,710 | 4/1993 | Perkins | 351/211 |
| 5,285,224 | 2/1994 | Sims | 351/235 |

FOREIGN PATENT DOCUMENTS

| | | |
|---|---|---|
| 1228434 | 11/1966 | Germany. |
| 991851 | 5/1965 | United Kingdom. |

OTHER PUBLICATIONS

Krimsky, Emanuel, "A Four-Way Sight Screener," *American Journal of Ophthalmology*, vol. 49, No. 1 (Jan. 1960), pp. 154–156.

Ketcham, Ferris F., "Modification of the Double Occluder," *American Journal of Ophthalmology*, vol. 72, No. 6 (Dec. 1971).

*Primary Examiner*—Huy Mai
*Attorney, Agent, or Firm*—Richard C. Litman

[57] ABSTRACT

A combination ophthalmic device includes various eye testing instruments in a single hand held device. The combination device is in the general configuration of a double ended occluder with an elongated central handle, but has different instruments at each end. One end has an occluder on one side thereof, with a fixation target instrument on the side opposite the occluder. The fixation target includes a plurality of characters each of a different size, and may be rotated to select an appropriate size target to test near visual acuity and other eye functions. The opposite end includes a Maddox rod instrument and a translucent red lens, each in its own circular enclosure. The red lens is used to test for diplopia (double vision), while the Maddox rod instrument is used to test for phoria, or correspondence between the two eyes. A plurality of pinholes is also provided to test visual acuity, with the pinholes being divided into two groups of different sized holes. The plurality of holes allows the subject to select the most convenient hole, and/or a hole of appropriate diameter for that person's acuity. Several scales are also provided along the handle portion between the two ends, for measuring other qualities or quantities associated with the eye. The present combination ophthalmic device thus combines several separate instruments into a single convenient device.

17 Claims, 3 Drawing Sheets

COMBINATION OPHTHALMIC DEVICE

BACKGROUND OF THE INVENTION

1. Field of the Invention

The present invention relates generally to instruments used in the field of medicine for patient examination, and more specifically to a combination ophthalmic device which includes several different ophthalmological examination instruments in a single device. The present device is hand held and includes only a single movable component therein, and is thus extremely economical to manufacture and purchase while still providing the benefit of several other instruments.

2. Description of the Prior Art

Medical science continues to develop various tests to determine the physical and mental condition of persons. Many of these tests are easily performed with relatively simple and non-invasive instrumentation. An example of a specialty in which such simple and non-invasive instruments are used commonly is in the field of ophthalmology, where hand held devices from simple occluders (covers used to cover one eye to test monocular vision) to Maddox rods (generally diagonally disposed translucent gratings used to test ocular orientation) and scales of various sorts are commonly used to test various characteristics of a person's vision.

In the past, some of these instruments, such as an occluder and linear scale disposed along the handle thereof, have been combined into a single device. However, with the relatively large number of simple tests which may be performed to check the visual health of a person, several instruments are still required, even where some of the instruments may have more than one function.

Accordingly, a need will be seen for a combination ophthalmic device which includes several non-invasive visual test instruments in a single device. The various functions of the device should be easily understood and used, and must also be less costly to purchase than the purchase of a plurality of other instruments which in combination are capable of providing the same functions. A discussion of the prior art of which the present inventor is aware, and its distinctions from the present invention, is provided below.

U.S. Pat. No. 1,158,187 issued on Oct. 26, 1915 to Henry L. De Zeng describes an Ophthalmological Instrument including a light source and a series of prisms and refracting lenses. The device is adapted to test the monocular focus of the eye, which test is beyond the scope of the present combination device. The De Zeng device does nothing to test rotary fixation, target pursuit, saccades, phoria, and various other conditions which may be tested using the present combination device.

U.S. Pat. No. 3,724,931 issued on Apr. 3, 1973 to Herbert J. Nevyas et al. describes a Lighting System Control For Ophthalmic Examinations. A series of ophthalmic instruments are arranged on a panel, with the removal of any one of the instruments automatically activating or controlling the lighting for that instrument and/or room lighting, as appropriate for the particular test to be performed. No specific tests or ophthalmic conditions are disclosed by Nevyas et al., and the electronic controls disclosed are beyond the scope of the present invention, which does not incorporate any electrical or electronic means in its operation.

U.S. Pat. No. 5,139,326 issued on Aug. 18, 1992 to Lloyd Snider describes a Disposable Occluder For Eye Examination, comprising a handle portion and occluder portion stamped from a single sheet of paper material. As the device is economically disposable after a single use, no lenses or additional features are provided by Snider, as provided by the present combination ophthalmic device.

U.S. Pat. No. 5,202,710 issued on Apr. 13, 1993 to David G. Perkins describes a Fixation Card Attachment For Retinoscope, comprising a magnetically attachable card which may be removably secured to a retinoscope having a suitable magnet therein. The fixation card provides only one of the features of the present combination ophthalmic device, and must rely upon another ophthalmic instrument for its operation, rather than being a self contained combination instrument as in the present invention.

U.S. Pat. No. 5,285,224 issued on Feb. 8, 1994 to Clinton N. Sims describes Methods And Apparatus For Determining Refractive Error, comprising two elongate frames each holding a series of lenses therein. The frames may be moved relative to one another, so different lenses from each frame are aligned with one another to allow the subject to select the optimum combination. Thus, the device is not so much an examination instrument as a means of testing for the proper corrective refraction in lieu of a series of test fittings of different glasses or the like. The Sims device is not adapted to test for the various conditions which may be tested using the present combination ophthalmic device.

British Patent Publication No. 991,851 published on May 12, 1965 describes Improvements In Or Relating To The Manufacture Of Ophthalmic Devices, comprising a mold for the manufacture of plastic lenses and a holder therefor. The resulting multiple lens holder and lenses cannot perform most of the functions of the present combination ophthalmic device, nor is the lens mold of the British publication intended or adapted to do so.

German Patent Publication No. 1,228,434 published on Nov. 10, 1966 illustrates a rack having a plurality of rotatable lenses therein, which may be collectively rotated by means of a pinion wheel at one end of the rack. The lenses are apparently asymmetric and the device functions as a lens fitting tool for astigmatic conditions. The device is thus somewhat similar to the device of the Sims U.S. Patent discussed further above, which also provided for the selective rotation of at least some lenses therein.

An article in the American Journal of Ophthalmology, vol. 49, no. 1 (Jan., 1960), pp. 154–156, titled "A Four-Way Sight Screener" by Emanuel Krimsky, M.D., describes a device having an occluder at one end of an elongate handle, and a combination red filter and Maddox rod instrument at the opposite end. The red filter and Maddox rod are each semicircular and share a circular opening in the end of the device, making them smaller, irregularly shaped and less convenient than a completely circular instrument. A single pinhole is provided. The present device provides a plurality of such pinholes in two groups of different diameters, for ease of alignment for the subject and to provide for differing uncorrected visual acuity between different subjects. The present combination device also has a rotary fixation dial at the occluder end and different scales, neither of which is disclosed by Krimsky in the American Journal of Ophthalmology article.

Finally, another article in the same journal, vol. 72, no. 6 (Dec., 1971), titled "Modification of the Double Occluder" by Ferris F. Ketcham, M.D. describes an instrument having an occluder at one end and Maddox rod at the opposite end of an elongated handle, similar to the four way sight screener of the article discussed above. However, no red filter or rotary fixation target dial is provided, and only a single pinhole is provided. The scales of the Ketcham occluder provide only a fraction of the functions of the present device.

None of the above inventions and patents, either singly or in combination, is seen to describe the instant invention as claimed.

SUMMARY OF THE INVENTION

Accordingly, it is a principal object of the invention to provide an improved combination ophthalmic device which comprises a generally central elongate handle with various ophthalmic instruments providing for multiple non-invasive tests at each end thereof.

It is another object of the invention to provide an improved ophthalmic device which includes an occluder and fixation target instrument on opposite sides of the device at one end thereof, which fixation target instrument is rotatable to provide different target sizes.

It is a further object of the invention to provide an improved ophthalmic device which includes a Maddox rod instrument and translucent red filter in separate openings at the second end of the handle portion, and a plurality of pinholes adjacent thereto for testing visual acuity.

An additional object of the invention is to provide an improved ophthalmic device which includes pinholes in two groups of different diameters for different levels of visual acuity.

Still another object of the invention is to provide an improved ophthalmic device having handle portion which includes a plurality of scales on each side thereof, providing for the measurement of different quantities or qualities during an examination.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
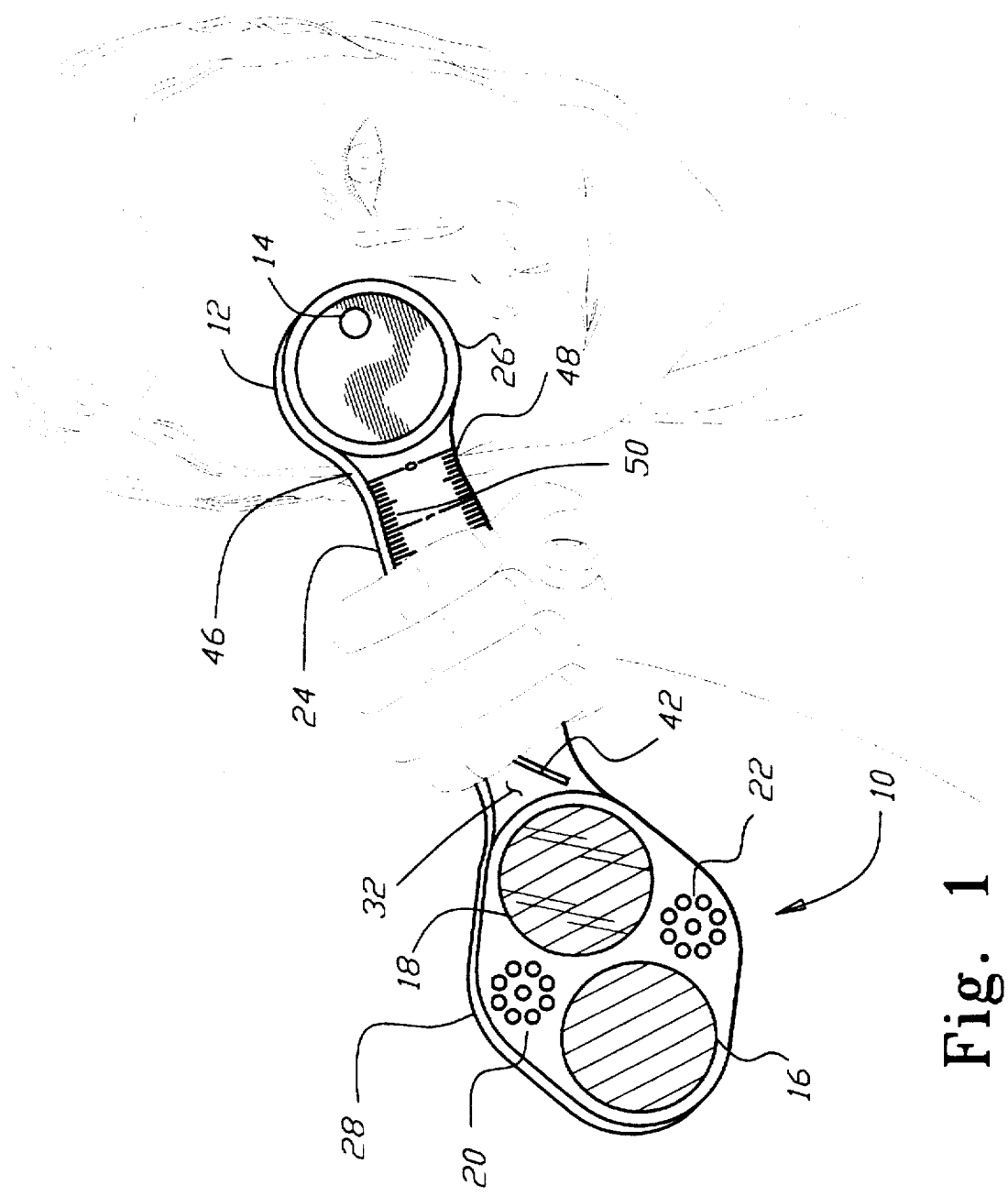
FIG. 1 is a front perspective view of the present combination ophthalmic device in use as an occluder, and showing many of its features.
Figure 2:
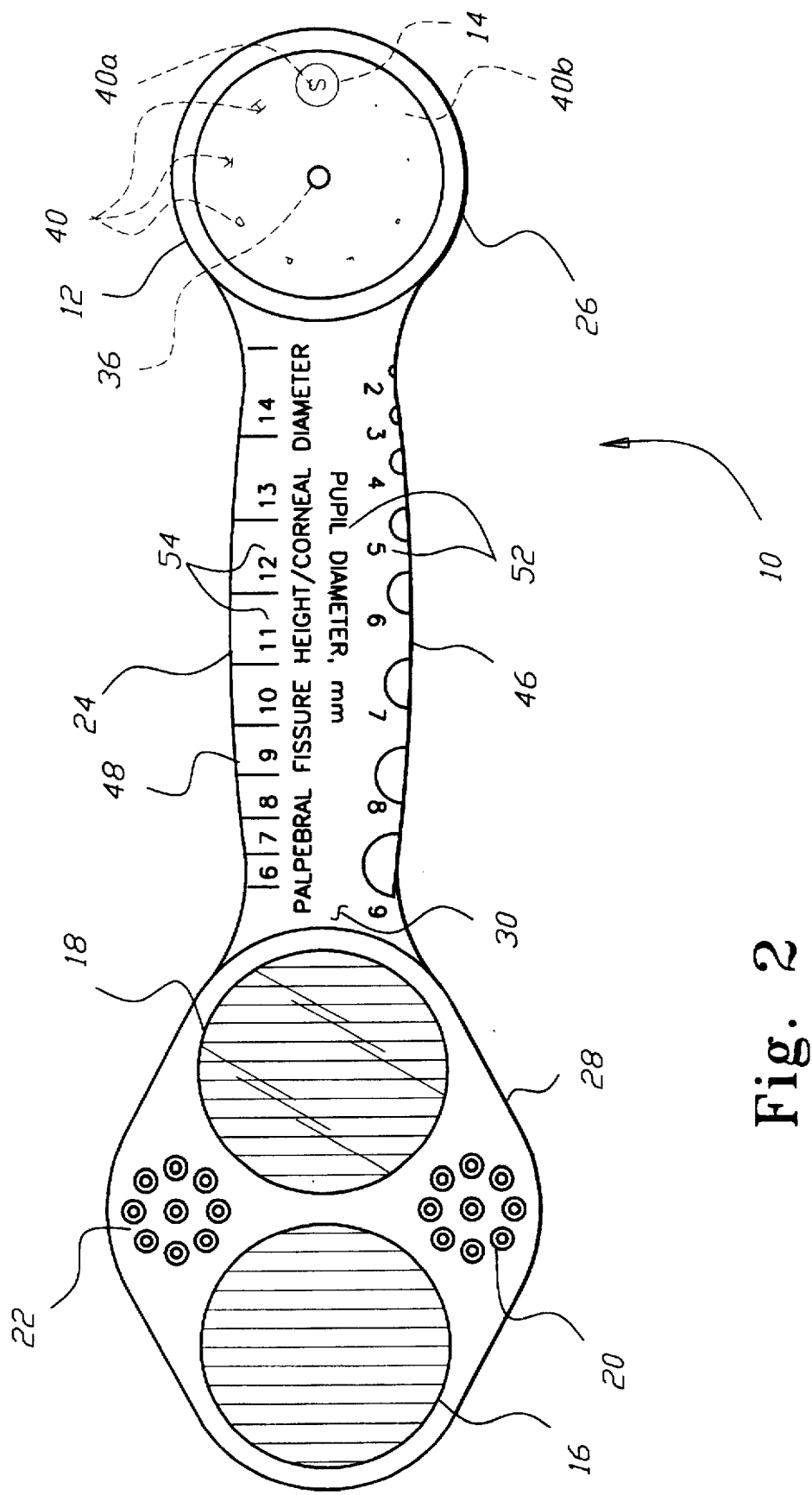
FIG. 2 is a rear elevation view of the device, disclosing additional features.

The present invention relates to a hand held, combination ophthalmic device 10, with its front view shown in FIG. 1 and the opposite rear view shown in FIG. 2. The ophthalmic device 10 provides a number of different ophthalmic instruments in a single hand held unit, thereby reducing the cost of purchasing several separate instruments and providing considerably more convenience by having all the related instruments at hand in a single, unitary device.

Standard ophthalmic examinations generally comprise several different non-invasive tests, which may be performed using the present device 10. These tests comprise pursuits, near cover, saccades, near point of convergence, near visual acuity, phoria, rapid measurement, sensory and motor fusion, occlusion, pinhole visual acuity, and a measurement of pupil diameter, interpupillary distance, and palpebral fissure height and corneal diameter. While multiple purpose instruments (either hand held devices or more complex electronic instruments) have been developed in the past, none of those instruments is capable of performing all of the above tests, as can the present hand held combination ophthalmic device 10 with its occluder portion 12, fixation target 14, circular Maddox rod window 16, circular translucent red filter window 18, pinhole aperture groups 20 and 22, and various scales disposed on a central elongate handle portion 24.

The present combination ophthalmic device 10 generally comprises the central handle portion 24, with a first instrument group 26 at a first end thereof, and an opposite second instrument group 28 at the opposite second end of the handle 24. The device 10 may be formed as a relatively thin, flat sheet of plastic or other material, with a first side 30 (FIG. 2) and an opposite second side 32 (FIG. 1). Preferably, the device 10 is black and opaque, with the exception of the translucent Maddox rod and red filter windows 16 and 18, in order to reduce light reflection during use. Other materials and colors may be used as desired.

The first instrument group 26 comprises a generally circular and opaque occluder 12, which is used to cover each eye in turn during an examination in order to check monocular vision and as an object to check binocular pursuit (i. e., the tracking of a moving object with the eyes), as well as near cover (monocular darkness adaptation), and other tests. As the entire first instrument group 26 is opaque, either side 30 or 32 may be used as the occluder 12. However, the fixation target aperture 14 is formed in the second side 32 of the device 10, while the first side 30 is essentially unbroken with the exception of the axle or pivot for the rotary fixation target wheel discussed below. Hence, it may be preferable to use the second side 32, opposite the fixation target aperture 14 in the first side 30, as the occluder 12 of the present combination ophthalmic device 10.

Figure 3:
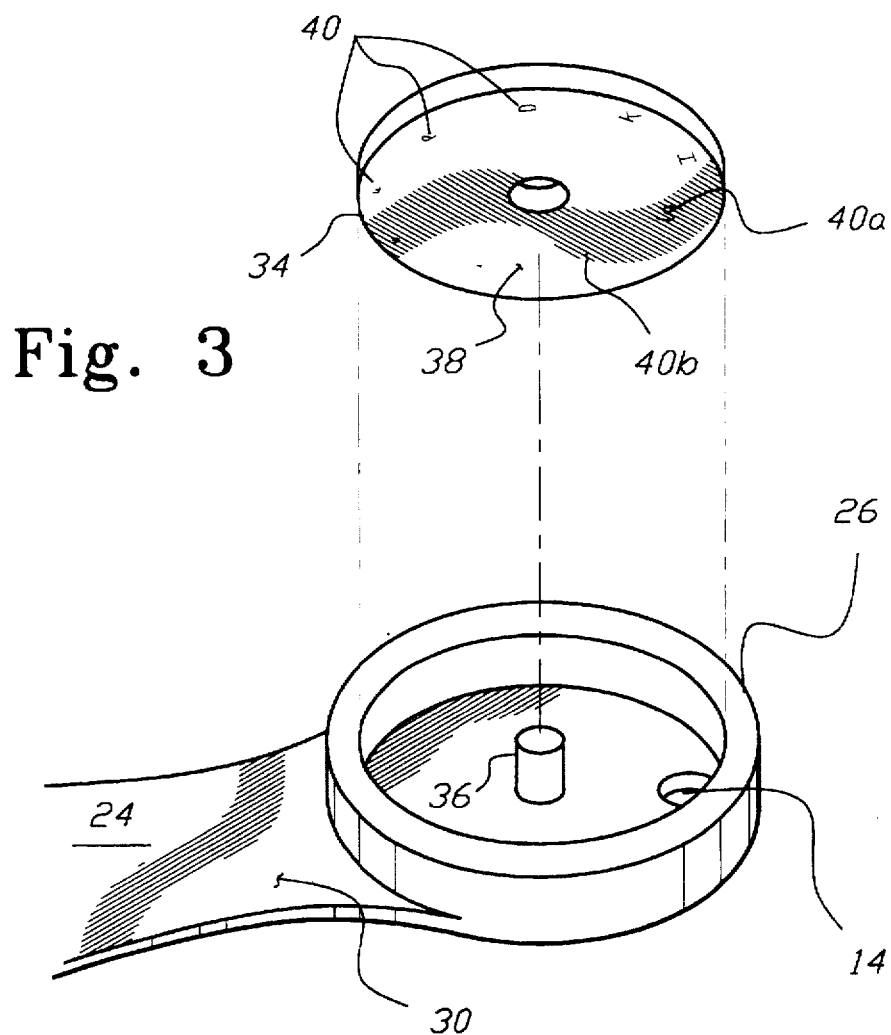
FIG. 3 is a fragmented and exploded perspective view of the rotary target fixation instrument of the present device, showing further details thereof.

The first instrument group end 26 includes a circular rotary target fixation wheel or dial 34 therein, which is shown from the occluder 12 or first side 30 of the device 10 in FIG. 2 in broken lines, and in the exploded view of FIG. 3. The dial 34 is secured by a central pivot or axle 36 extending toward the second side 32 of the device 10. (It should be understood that the outer end of this pivot 36 does not protrude substantially above the outermost surface of the target fixation dial 34, in order to obviate any potential injury as that surface is placed adjacent to the eye for use as an occluder 12.) The fixation target dial 34 has an inner face 38 including a plurality of symbols 40 (alphanumeric, graphic, etc., as desired) in a generally radial array from the central pivot 36. These symbols 40 are of various sizes ranging from 0.4 millimeter to four millimeters (other sizes may be provided alternatively), and are placed in order about the inner face 38 of the dial 34, from a largest symbol 40a to a smallest symbol 40b.

These symbols 40 are selectively individually visible through the fixation target aperture 14, which extends through the second side 32 of the first instrument group end 26 of the device 10. Rotating the dial 34 enables one to select any size symbol 40, from a smallest symbol 40b to a largest symbol 40a. This permits numerous vision tests to be performed, such as target fixation and saccades (rapid accommodation to different target sizes and different points in the visual field), near visual acuity, near point of convergence, etc.

The opposite second instrument group 28 comprises several ophthalmic instruments in a generally coplanar array, including a generally circular Maddox rod window 16, a generally circular translucent red filter 18, and two groups of pinhole apertures 20 and 22, with each aperture group 20 and 22 comprising a plurality of apertures each having the same diameter in each group, with the apertures of the different groups having different diameters. Each of these instruments 16 through 22 is transparent, translucent, or an open passage, and thus they cannot be concentric with one another, as in the case of the rotary fixation target dial 34 and occluder 12 of the first instrument group end 26.

The Maddox rod window 16 may be formed conventionally as a plurality of parallel transparent or translucent rods, a translucent diffraction grating of parallel lines, etc. This window 16 will cause a pinpoint light source to appear as a line normal to the orientation of the rods or lines of the window, 16 when the light is viewed through the window 16. An orientation mark 42, indicating the orientation of the light line viewed through the window 16, is preferably provided near the second instrument group end 28 of the device 10. This instrument 16 may be used to test for phoria (alignment of the visual focal axis), which includes conditions such as strabismus and other phorias where the focal axes of the two eyes are not in alignment, either vertically or horizontally, as well as other tests.

The translucent red filter 18 is used for related tests, such as diplopia (double vision). By using a white light source and a red filter window 18 in front of one eye, any divergence of the two light colors reported by the subject, in any axis, is indicative of some form of diplopia. The placement of these two instruments (the Maddox rod window 16 and red filter window 18) adjacent one another in the second instrument group, enables the subject or examining person to move quickly from one of the instruments 16 or 18 to the other, with no need to turn the combination device 10 from end to end or from the first side to the second side.

Another instrument type disposed in the second instrument group 28, comprises two groups of pinhole apertures 20 and 22, with the apertures 20 having a smaller diameter than the apertures 22. While a single aperture 20 or 22 could be used, the provision of multiple apertures 20 and 22 makes it easier for the subject to find a specific aperture 20 or 22 which aligns precisely with his or her focal axis when sighting through the aperture 20/22. The purpose of the different diameters of the apertures of the two aperture groups 20/22 is to provide apertures 20 having a smaller diameter for subjects with clear vision, and apertures 22 having a larger diameter to provide more light for subjects with obscured vision (cataracts or the like). The pinhole apertures 20/22 provide a test of visual acuity to determine whether the subject's vision might be corrected with corrective lenses, by means of the "pinhole camera" effect, wherein a sufficiently small light passage relative to the focal length provides a relatively sharp image.

Figure 4:
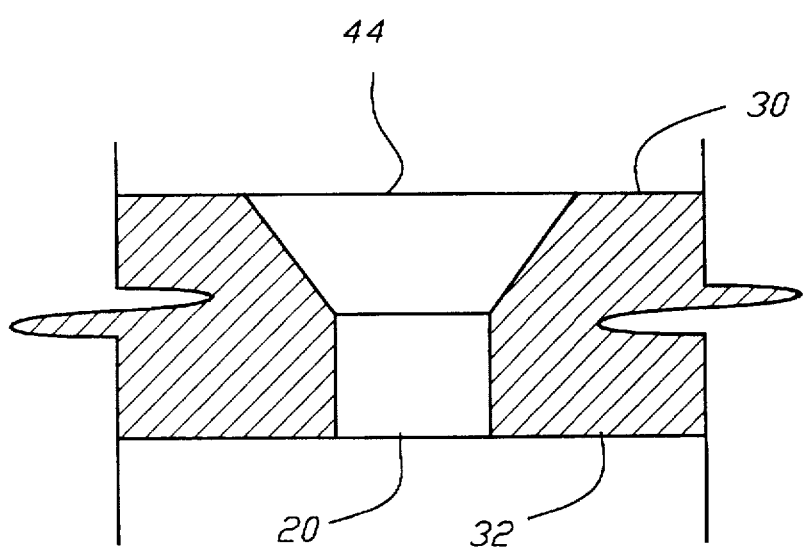
FIG. 4 is a fragmented detail elevation view in section of one of the pinholes of the present device, showing further details of its construction.

A conical taper 44 is provided in each of the apertures 20 and 22, in the first side 30 of the device 10, as shown in detail in FIG. 4. (While only one aperture 20 is shown in FIG. 4, it will be understood that FIG. 4 is exemplary and that the taper 44 is provided for each of the apertures 20 and 22.) This taper 44 is preferably placed adjacent the subject's eye when sighting through one of the apertures 20/22, and serves to reduce light reflections within the apertures 20/22 which might effect the results of the pinhole visual acuity test. The apertures 20/22 are relatively small, with the smaller apertures 20 having a diameter on the order of one millimeter and the larger apertures 22 having a diameter some thirty percent larger, or on the order of 1.3 millimeter with the maximum diameter of the conical taper being proportional. Alternative diameters may be used to suit particular requirements.

The handle portion 24 includes a plurality of scales, which may be used to measure or determine certain ophthalmic characteristics of a subject. The handle portion 24 includes a first edge 46 and an opposite second edge 48, with various scales being aligned along those edges 46 and 48. The second side 32 of the handle portion 24, shown in FIG. 1, includes a double metric scale 50 marked along both the first edge 46 and the opposite second edge 48, thereby enabling the combination ophthalmic device 10 to be used to provide linear measurements in either direction along the handle portion 24. These metric scales 50 may be used to measure the interpupillary distance of a subject for the fitting of glasses, or for other purposes as desired.

The opposite first side 30 of the handle portion 24, shown in FIG. 2, includes two different scales. A pupil diameter scale 52, comprising a series of semicircular arcs with their diameters indicated in millimeters, is provided along the first edge 46 of the first side 30 of the handle portion 24 of the device 10. An examiner may compare the apparent pupil size of the subject with the semicircular arcs of the pupil diameter scale 52, to arrive at a reasonably accurate estimate of the subject pupil diameter.

A second scale 54 is provided along the opposite second edge 48 of the first side 30 of the handle portion 24. This scale 54 is a combination palpebral fissure height and corneal diameter scale, and is used to check the distance between the lowermost point of the upper edge of the lower eyelid and the uppermost point of the lower edge of the upper eyelid (palpebral fissure height) and the diameter of the cornea. This is done by comparison with the scale 54, similar to the use of the pupil diameter scale 52.

In summary, the present combination ophthalmic device 10 will be seen to provide an extremely handy tool which may be used to test or check numerous qualities and quantities of a subject or patient during an examination. The device 10 is quite easy to use by a skilled practitioner, due to the non-invasive nature of the tests performed. All such tests may be performed relatively quickly, due to the convenience of having multiple instruments readily at hand, thus resulting in some saving of time on the part of both the examiner and subject, and some potential economy for the subject in the reduction of time required for an examination. The economy of the present device extends to the purchaser also, as the present combination ophthalmic device 10 is considerably more economical to manufacture, and thus to purchase, than a collection of instruments or devices capable of accomplishing all of the functions of the present device.

It is to be understood that the present invention is not limited to the sole embodiment described above, but encompasses any and all embodiments within the scope of the following claims.

I claim:

1. A hand held combination ophthalmic device, comprising:

a generally central, elongate handle portion having a first end and an opposite second end, with said first end of said handle portion having a first instrument group extending therefrom, and said second end of said handle portion having a second instrument group extending therefrom;

said ophthalmic device having a first side and an opposite second side, with said first instrument group including a plurality of ophthalmic instruments disposed concentrically therein and said second instrument group including a plurality of generally coplanar ophthalmic instruments disposed therein, and;

said handle portion including a plurality of different scales disposed upon said first side and said second side thereof.

2. The combination ophthalmic device according to claim 1, wherein:

said first instrument group includes a generally circular occluder disposed within said first side of said first end of said ophthalmic device.

3. The combination ophthalmic device according to claim 1, wherein:

said first instrument group includes a fixation target disposed within said second side of said first end of said ophthalmic device.

4. The combination ophthalmic device according to claim 3, wherein:

said first side of said first end of said ophthalmic device includes a rotary dial having an inner face with a plurality of symbols disposed generally radially thereabout, with said symbols being arranged in order of decreasing size from a largest one of said symbols to a smallest one of said symbols, and;

said fixation target comprises an aperture formed through said second side of said first end of said ophthalmic device and radially offset from the center thereof, with one of said symbols of said rotary dial being selectively aligned with said fixation target aperture to be visible therethrough to test near visual acuity using said ophthalmic device.

5. The combination ophthalmic device according to claim 1, wherein:

said second instrument group includes a generally circular Maddox rod window disposed therethrough.

6. The combination ophthalmic device according to claim 1, wherein:

said second instrument group includes a generally circular translucent red filter disposed therethrough.

7. The combination ophthalmic device according to claim 1, wherein:

said second instrument group includes a plurality of pinhole apertures formed therethrough.

8. The combination ophthalmic device according to claim 7, wherein:

said pinhole apertures comprise a first group and a separate second group, with said apertures of said first group each having a smaller diameter than said apertures of said second group.

9. The combination ophthalmic device according to claim 7, wherein:

each of said pinhole apertures includes a conical taper formed in said first side of said ophthalmic device, so that said apertures each have a larger diameter at said first side than at said second side of said ophthalmic device.

10. The combination ophthalmic device according to claim 1, wherein:

said handle portion of said ophthalmic device includes a first edge and an opposite second edge, with said handle portion including a double metric scale disposed upon said second side and along said first edge and said second edge of said handle portion, a pupil diameter scale disposed upon said first side and along said first edge of said handle portion, and a palpebral fissure height and cornea diameter scale disposed upon said first side and along said second edge of said handle portion.

11. The combination ophthalmic device according to claim 1, wherein:

said ophthalmic device is formed of opaque black plastic, excepting said Maddox window and said translucent red filter of said second instrument group.

12. A hand held combination ophthalmic device comprising:

a generally central, elongate handle portion having a first end and an opposite second end, with said first end of said handle portion having a first instrument group extending therefrom, and said second end of said handle portion having a second instrument group extending therefrom;

said ophthalmic device having a first side and an opposite second side, with said first instrument group including an occluder and a fixation target disposed concentrically therein and said second instrument group including a Maddox window, a translucent red filter, and a plurality of pinhole apertures disposed generally coplanar therein, and;

a plurality of scales being disposed upon said first side and said second side of said handle portion.

13. The combination ophthalmic device of claim 12, wherein:

said occluder includes a rotary dial having an inner face with a plurality of symbols disposed generally radially thereabout, with said symbols being arranged in order of decreasing size from a largest one of said symbols to a smallest one of said symbols, and;

said fixation target comprises an aperture formed through said first end of said ophthalmic device opposite said occluder and radially offset from the center thereof, with one of said symbols of said rotary dial being selectively aligned with said fixation target aperture to be visible therethrough to test near visual acuity using said ophthalmic device.

14. The combination ophthalmic device according to claim 12 wherein:

said handle portion of said ophthalmic device includes a first edge and an opposite second edge, with said handle portion including a double metric scale disposed upon said second side and along said first edge and said second edge of said handle portion, a pupil diameter scale disposed upon said first side and along said first edge of said handle portion, and a palpebral fissure height and cornea diameter scale disposed upon said first side and along said second edge of said handle portion.

15. The combination ophthalmic device according to claim 12, wherein:

said pinhole apertures comprise a first group and a separate second group, with said apertures of said first group each having a smaller diameter than said apertures of said second group.

16. The combination ophthalmic device according to claim 15, wherein:

each of said pinhole apertures includes a conical taper formed in said first side of said ophthalmic device, so that said apertures each have a larger diameter at said first side than at said second side of said ophthalmic device.

17. The combination ophthalmic device according to claim 12, wherein:

said ophthalmic device is formed of opaque black plastic, excepting said Maddox window and said translucent red filter.

* * * * *